United States Patent
Lombardi

(10) Patent No.: US 9,009,933 B2
(45) Date of Patent: Apr. 21, 2015

(54) METHOD TO IMPROVE THE APPEARANCE OF A CORPSE AND NEW THANATOCOSMETIC COMPOSITIONS

(75) Inventor: Astrid Lombardi, Rezzato (IT)

(73) Assignee: Astrid Lombardi, Rezzato (IT)

( * ) Notice: Subject to any disclaimer, the term of this patent is extended or adjusted under 35 U.S.C. 154(b) by 307 days.

(21) Appl. No.: 13/364,509

(22) Filed: Feb. 2, 2012

(65) Prior Publication Data

US 2013/0199007 A1   Aug. 8, 2013

(51) Int. Cl.
*A01N 1/00* (2006.01)
*C08L 5/16* (2006.01)

(52) U.S. Cl.
CPC .... *A01N 1/00* (2013.01); *C08L 5/16* (2013.01)

(58) Field of Classification Search
USPC .......... 604/289, 290, 359, 360; 424/455, 725, 424/736, 748, 753, 764, 776, 777
See application file for complete search history.

(56) References Cited

U.S. PATENT DOCUMENTS

2008/0044364 A1\*  2/2008  Carola et al. .................... 424/59
2010/0292268 A1\*  11/2010  Mosher et al. ................ 514/301

\* cited by examiner

*Primary Examiner* — Melanie Hand
(74) *Attorney, Agent, or Firm* — Nixon & Vanderhye P.C.

(57) ABSTRACT

The present invention relates to a method to improve the appearance of a corpse by means of the application of specific thanatocosmetic compositions. The invention also relates to the new compositions and to their use in thanato-aesthetics.

9 Claims, No Drawings

METHOD TO IMPROVE THE APPEARANCE OF A CORPSE AND NEW THANATOCOSMETIC COMPOSITIONS

DESCRIPTION OF THE INVENTION

According to one aspect thereof, the invention relates to a method to improve the appearance of a corpse which comprises the steps of:

a. applying to the skin of the corpse a deodorizing composition comprising at least one compound selected from *thymus vulgaris* oil, *ahnfeltia concinna* extract, *melissa officinalis* oil, myrrh extract, fenugreek extract, lemon oil and honeysuckle oil; and subsequently b. applying to the skin of the corpse at least one composition selected from:

b'. a composition with relaxing effect which comprises hydroxypropyl cyclodextrin; and b" one or more compositions with draining effect and capable of camouflaging abnormal pigmentation of the skin of the corpse, said compositions comprising: at least one compound selected from caffeine, escin, *helianthus annulus* seed oil, *hedera helix* extract, *arctostaphylos uva ursi* extract, *tilia tomentosa* extract; and a colouring compound selected from CI 14700, CI 42090 or a mixture of CI 42090 and CI 19140.

According to a preferred embodiment of the invention, the moisturizing and deodorizing composition of step (a) comprises at least two of the compounds indicated and even more preferably comprises the compounds *thymus vulgaris* oil, *ahnfeltia concinna* extract and *melissa officinalis* oil.

According to another preferred embodiment of the invention, the composition with deodorizing effect of step (a) also comprises moisturizing agents.

According to a preferred embodiment of the invention, the composition with relaxing effect of step (b") comprises at least two or three of the compounds indicated and even more preferably comprises all the compounds caffeine, escin, *helianthus annulus* seed oil, *hedera helix* extract, *arctostaphylos uva ursi* extract, *tilia tomentosa* extract. The colorants indicated above are added to these compositions to obtain also a camouflaging effect when used in the presence of abnormal colouring of the skin of the corpse.

Advantageously, the compositions used in the method of the invention are in the form of emulsions suitable to be applied to the skin and also comprise other components selected from the cosmetic agents conventionally used in the cosmetic art, for example selected from water, glycerin, emollients such as ethylhexyl palmitate, emulsifiers such as cetearyl alcohol, surfactants such as ceteareth-25, preservatives, etc.

The compositions used in steps (a) and (b) of the invention are new and constitute a further aspect of the invention, as does their use in thanato-aesthetics.

According to a particularly preferred embodiment of the invention, the moisturizing and deodorizing composition of step (a) comprises *thymus vulgaris* oil in an amount of 0.1-2%, advantageously around 0.5%, *ahnfeltia concinna* extract in the amount of 0.5-5%, advantageously around 2%, and *melissa officinalis* oil in the amount of 0.05-0.5%, advantageously around 0.1%.

According to a particularly preferred embodiment of the invention, the composition with relaxing effect of step (b') comprises a 60% aqueous solution of hydroxypropyl cyclodextrin, in the amount of 0.5-5%, advantageously around 1%.

According to a particularly preferred embodiment of the invention, the composition with relaxing effect of step (b") comprises caffeine in the amount of 1-5%, advantageously around 3%, escin in the amount of 0.1-3%, advantageously around 1%, *helianthus annulus* seed oil in the amount of 0.1-1%, advantageously around 0.5%, *hedera helix* extract in the amount of 0.5-5%, advantageously around 2%, *arctostaphylos uva ursi* extract in the amount of 0.5-5%, advantageously around 2%, *tilia tomentosa* extract in the amount of 0.5-5%, advantageously around 2%.

Unless otherwise indicated, the percentages indicated herein are intended by weight, relative to the total weight of the composition.

According to a preferred embodiment, the colouring compounds CI 14700 and CI 42090 or the mixture of CI 42090 and CI 19140 are added to the composition of step (b") in the form of solution, for example solution in water with the optional addition of ethylhexylglycerin and/or phenoxyethanol, and are present in the composition in an amount sufficient to provide the composition with the desired colouring effect.

In particular, the colouring compound CI 14700 provides the composition with a red colouring, the colouring compound CI 42090 with a blue colouring and the mixture of CI 42090 and CI 19140 with a green colouring.

Preferred compositions representative of the invention are set forth in the experimental section of the present description.

The method of the invention is carried out as follows.

The composition of step (a) is applied to the face, hands and, if necessary, also to the rest of the body of the corpse and the composition is massaged delicately.

Subsequently, one or more compositions of step (b) can be applied to the face or to the body of the corpse. In particular, the composition of step (b') shall be applied to the parts of the body that are to appear to be relaxed, for example in the case of muscle contraction or hollowing or excessive relaxation of tissue due to excessive weight loss, etc.

In addition or alternatively to the composition of step (b'), one or more of the compositions of step (b") can be applied.

In the case of wishing to camouflage the pathological presence of the colour red, the composition of step (b") containing the mixture of CI 42090 and CI 19140 can be applied, as this has a green colouring that covers abnormal red pigmentation.

In the case of wishing to camouflage the pathological presence of the colour yellow or green, the composition of step (b") containing the CI 42090 can be applied, as this has a blue colouring that covers abnormal yellow/green pigmentation.

Finally, in the case of wishing to camouflage the pathological presence of the colour blue, the composition of step (b") containing CI 14700 can be applied, as this has a red colouring that covers abnormal blue pigmentation.

It is evident that several compositions can be applied to different parts of the body of the corpse according to need and to the effect wished to be produced.

EXPERIMENTAL SECTION

Example 1

| TRADE NAME | % by weight | INCI NAME |
|---|---|---|
| Deodorizing moisturizing composition | | |
| Ceteareth 25 | 3 | CETEARETH-25 |
| Laurex cs | 8 | CETEARYL ALCOHOL |

Deodorizing moisturizing composition

| TRADE NAME | % by weight | INCI NAME |
|---|---|---|
| Saboderm | 10 | ETHYLHEXYL PALMITATE |
| Water | q.s. to 100 | AQUA (WATER) |
| Glycerin | 5 | GLYCERIN |
| Sequamin 2 | 0.1 | DISODIUM EDTA |
| Antiphlogistic | 1 | AQUA (WATER) PROPYLENE GLYCOL PHANTENOL ALLANTOIN GLYCYRRHETINIC ACID |
| arginine | 0.1 | ARGININE |
| Isocide BAS | 1 | BENZYL ALCOHOL DEHYDROACETIC ACID AQUA(WATER) |
| Phytodermina c | 1 | PROPYLENE GLYCOL (% B) AQUA (WATER) (% B) HYDROLYZED SOY PROTEIN (% E) |
| Plantadesamido | 2 | AQUA (WATER) SODIUM LACTATE *AHNFELTIA CONCINNA* EXTRACT HYDROXYPROLINE |
| *Melissa* essential oil | 0.1 | *MELISSA OFFICINALIS* (LEMON BALM OIL) |
| Thyme essential oil | 0.5 | *THYMUS VULGARIS* (THYME OIL) |

Example 2

Relaxing composition with myorelaxant-like effect

| TRADE NAME | % by weight | INCI NAME |
|---|---|---|
| CETEARETH 25 | 2 | CETEARETH-25 |
| LAUREX CS | 8 | CETEARYL ALCOHOL |
| SABODERM OP | 10 | ETHYLHEXYL PALMITATE |
| DISTILLED WATER | q.s. to 100 | AQUA (WATER) |
| Sequamin 2 | 0.1 | DISODIUM EDTA |
| 60% aqueous solution of hydroxypropyl cyclodextrin | 1 | AQUA (WATER) HYDROXYPROPYL CYCLODEXTRIN |
| Isocide BAS | 1 | BENZYL ALCOHOL DEHYDROACETIC ACID AQUA(WATER) |
| VIT. E ACETATE | 0.1 | TOCOPHERYL ACETATE |
| Glycerin | 5 | GLYCERIN |

Example 3

Red draining composition

| TRADE NAME | % by weight | INCI NAME |
|---|---|---|
| Ceteareth 25 | 3 | CETEARETH-25 |
| Laurex cs | 8 | CETEARYL ALCOHOL |
| Saboderm | 10 | ETHYLHEXYL PALMITATE |
| Water | q.s. to 100 | AQUA (WATER) |
| Glycerin | 5 | GLYCERIN |
| Sequamin 2 | 0.1 | DISODIUM EDTA |
| Caffeine | 3 | CAFFEINE |
| Escin | 1 | ESCIN |
| Vitamin A | 0.5 | RETINYL ACETATE *HELIANTHUS ANNULUS* (SUNFLOWER) SEED OIL |
| Isocide BAS | 1 | BENZYL ALCOHOL DEHYDROACETIC ACID AQUA(WATER) |
| Ivy extract | 2 | PROPYLENE GLYCOL AQUA (WATER) *HEDERA HELIX* (IVY) EXTRACT |
| *Uva ursi* extract | 2 | PROPYLENE GLYCOL AQUA (WATER) ARCTOSTAPHYLOS *UVA URSI* EXTRACT (ARCTOSTAPHYLOS *UVA URSI LEAF* EXTRACT) |
| *Tilia tomentosa* extract | 2 | PROPYLENE GLYCOL AQUA (WATER) *TILIA TOMENTOSA* EXTRACT |
| Clay | 1 | KAOLIN |
| Red pigments | 1 | TITANIUM DIOXIDE MIXTURE OF PIGMENTS MICA SILICA DIMETHYL SILYLATE |
| Pink solution | q.s. | AQUA (WATER) CI 14700 (FOOD RED 1-FD&C RED N.4) PHENOXYETHANOL (89-90%) ETHYLHEXYLGLYCERIN (9-11%) |

Example 4

Blue draining composition

| TRADE NAME | % by weight | INCI NAME |
|---|---|---|
| Ceteareth 25 | 3 | CETEARETH-25 |
| Laurex cs | 8 | CETEARYL ALCOHOL |
| Saboderm | 10 | ETHYLHEXYL PALMITATE |
| Water | q.s. to 100 | AQUA (WATER) |
| Glycerin | 5 | GLYCERIN |
| Sequamin 2 | 0.1 | DISODIUM EDTA |
| Caffeine | 3 | CAFFEINE |
| Escin | 1 | ESCIN |
| Vitamin A | 0.5 | RETINYL ACETATE *HELIANTHUS ANNULUS* (SUNFLOWER) SEED OIL |
| Isocide BAS | 1 | BENZYL ALCOHOL DEHYDROACETIC ACID AQUA(WATER) |
| Ivy extract | 2 | PROPYLENE GLYCOL AQUA (WATER) *HEDERA HELIX* (IVY) EXTRACT |
| *Uva ursi* extract | 2 | PROPYLENE GLYCOL AQUA (WATER) ARCTOSTAPHYLOS *UVA URSI* EXTRACT (ARCTOSTAPHYLOS *UVA URSI LEAF* EXTRACT) |
| *Tilia tomentosa* extract | 2 | PROPYLENE GLYCOL AQUA (WATER) *TILIA TOMENTOSA* EXTRACT |
| Clay | 1 | KAOLIN |
| Blue pigments | 1 | TITANIUM DIOXIDE MIXTURE OF PIGMENTS MICA SILICA DIMETHYL SILYLATE |
| Blue solution | q.s. | AQUA (WATER) CI 42090 (BLUE-FD&C BLUE N.1 W092) PHENOXYETHANOL (89-90%) ETHYLHEXYLGLYCERIN (9-11%) |

Example 5

Green draining composition

| TRADE NAME | % by weight | INCI NAME |
|---|---|---|
| Ceteareth 25 | 3 | CETEARETH-25 |
| Laurex cs | 8 | CETEARYL ALCOHOL |

-continued

Green draining composition

| TRADE NAME | % by weight | INCI NAME |
|---|---|---|
| Saboderm | 10 | ETHYLHEXYL PALMITATE |
| Water | q.s. to 100 | AQUA (WATER) |
| Glycerin | 5 | GLYCERIN |
| Sequamin 2 | 0.1 | DISODIUM EDTA |
| Caffeine | 3 | CAFFEINE |
| Escin | 1 | ESCIN |
| Vitamin A | 0.5 | RETINYL ACETATE *HELIANTHUS ANNULUS* (SUNFLOWER) SEED OIL |
| Isocide BAS | 1 | BENZYL ALCOHOL DEHYDROACETIC ACID AQUA(WATER) |
| Ivy extract | 2 | PROPYLENE GLYCOL AQUA (WATER) *HEDERA HELIX* (IVY) EXTRACT |
| *Uva ursi* extract | 2 | PROPYLENE GLYCOL AQUA (WATER) ARCTOSTAPHYLOS *UVA URSI* EXTRACT (ARCTOSTAPHYLOS *UVA URSI* LEAF EXTRACT) |
| *Tilia tomentosa* extract | 2 | PROPYLENE GLYCOL AQUA (WATER) *TILIA TOMENTOSA* EXTRACT |
| Clay | 1 | KAOLIN |
| Green pigments | 1 | TITANIUM DIOXIDE MIXTURE OF PIGMENTS MICA SILICA DIMETHYL SILYLATE |
| Green solution | q.s. | AQUA (WATER) CI 42090 (BLUE-FD&C BLUE N.1 W092) CI 19140 (ACID YELLOW 23-FD&C YELLOW NO 5) PHENOXYETHANOL (89-90%) ETHYLHEXYLGLYCERIN (9-11%) |

The invention claimed is:

1. A method to improve the appearance of a corpse which comprises in sequence the steps of:
   a. applying to the skin of the corpse a deodorizing composition comprising at least one compound selected from *thymus vulgaris* oil, *ahnfeltia concinna* extract, *melissa officinalis* oil, myrrh extract, fenugreek extract, lemon oil and honeysuckle oil; and subsequently
   b. applying to the skin of the corpse at least one composition selected from
      b'. a composition with relaxing effect which comprises hydroxypropyl cyclodextrin; and
      b''. one or more compositions with draining effect and capable of camouflaging abnormal pigmentation of the skin of the corpse, said compositions comprising
         at least one compound selected from caffeine, escin, *helianthus* annulus seed oil, *hedera helix* extract, *arctostaphylos uva ursi* extract, *tilia tomentosa* extract; and
         a colouring compound selected from CI 14700, CI 42090 or a mixture of CI 42090 and CI 19140.

2. The method according to claim 1, wherein the moisturizing and deodorizing composition of step (a) comprises *thymus vulgaris* oil, *ahnfeltia concinna* extract and *melissa officinalis* oil.

3. The method according to claim 1, wherein the deodorizing composition of step (a) also comprises moisturizing agents.

4. The method according to claim 1, wherein the composition with relaxing effect of step (b'') comprises caffeine, escin, *helianthus annulus* seed oil, *hedera helix* extract, *arctostaphylos uva ursi* extract, *tilia tomentosa* extract.

5. A thanato-aesthetic composition which comprises caffeine, escin, *helianthus annulus* seed oil, *hedera helix* extract, *arctostaphylos uva ursi* extract, *tilia tomentosa* extract, and a colouring compound selected from CI 14700; CI 42090; and a mixture of CI 42090 and CI 19140.

6. A method for obtaining a draining effect and camouflage abnormal pigmentations of the skin of a corpse which comprises applying the composition of claim 5.

7. The method according to claim 2, wherein the deodorizing composition of step (a) also comprises moisturizing agents.

8. The method according to claim 2, wherein the composition with relaxing effect of step (b'') comprises caffeine, escin, *helianthus annulus* seed oil, *hedera helix* extract, *arctostaphylos uva ursi* extract, *tilia tomentosa* extract.

9. The method according to claim 3, wherein the composition with relaxing effect of step (b'') comprises caffeine, escin, *helianthus annulus* seed oil, *hedera helix* extract, *arctostaphylos uva ursi* extract, *tilia tomentosa* extract.

* * * * *